US012558556B2

(12) United States Patent
Felix et al.

(10) Patent No.: US 12,558,556 B2
(45) Date of Patent: Feb. 24, 2026

(54) DEFIBRILLATOR

(71) Applicant: Bardy Technologies, Inc., Bellevue, WA (US)

(72) Inventors: Jason Felix, Vashon Island, WA (US); Gust H. Bardy, Carnation, WA (US)

(73) Assignee: Bardy Technologies, Inc., Bellevue, WA (US)

( * ) Notice: Subject to any disclaimer, the term of this patent is extended or adjusted under 35 U.S.C. 154(b) by 0 days.

(21) Appl. No.: 19/272,673

(22) Filed: Jul. 17, 2025

(65) Prior Publication Data

US 2026/0048270 A1 Feb. 19, 2026

Related U.S. Application Data

(63) Continuation of application No. 19/018,895, filed on Jan. 13, 2025, now Pat. No. 12,440,693, which is a continuation of application No. 18/806,524, filed on Aug. 15, 2024, now Pat. No. 12,280,265.

(51) Int. Cl.
*A61N 1/39* (2006.01)
*A61N 1/02* (2006.01)
*A61N 1/04* (2006.01)

(52) U.S. Cl.
CPC .......... *A61N 1/3931* (2013.01); *A61N 1/025* (2013.01); *A61N 1/39046* (2017.08); *A61N 1/3956* (2013.01); *A61N 1/3981* (2013.01); *A61N 1/0408* (2013.01); *A61N 1/3937* (2013.01); *A61N 1/3993* (2013.01)

(58) Field of Classification Search
None
See application file for complete search history.

(56) References Cited

U.S. PATENT DOCUMENTS

| | | | |
|---|---|---|---|
| 5,040,534 A | 8/1991 | Mann et al. | |
| 5,713,925 A * | 2/1998 | Sullivan ............... | A61N 1/3931 |
| | | | 607/148 |
| 5,868,794 A | 2/1999 | Barkley | |
| 6,556,864 B1 | 4/2003 | Picardo | |
| 7,848,804 B1 | 12/2010 | Kroll | |
| 2002/0133197 A1 | 9/2002 | Snyder et al. | |
| 2003/0028219 A1 | 2/2003 | Powers et al. | |
| 2003/0181950 A1 | 9/2003 | Powers | |

(Continued)

*Primary Examiner* — Mallika D Fairchild
(74) *Attorney, Agent, or Firm* — Leonid Kisselev

(57) ABSTRACT

A defibrillator is provided. The defibrillator includes: one or more power generation subcircuits configured to generate a variable voltage bias supply; a solid-state defibrillation waveform therapy generator circuit including a plurality of elements at least portion of which is configured to be driven by the variable voltage bias supply, the generator configured to: generate one or more defibrillation waveforms when the voltage is in a high energy state, activating at least some of the elements of the generator in the saturated region; and generate one or more internal discharge waveforms that are isolated from the patient when the voltage is in a low energy state, activating at least some of the elements of the generator in the transconductance region and dissipating energy as heat; and a microcontroller control unit configured to control whether the voltage supply is provided to the generator circuit at the high or low energy state.

16 Claims, 11 Drawing Sheets

(56) References Cited

U.S. PATENT DOCUMENTS

| | | | |
|---|---|---|---|
| 2004/0002736 A1* | 1/2004 | Waltman | A61N 1/3968 607/5 |
| 2006/0111748 A1 | 5/2006 | Bucher | |
| 2008/0287589 A1 | 11/2008 | Ounaies et al. | |
| 2010/0022904 A1 | 1/2010 | Centen | |
| 2010/0114236 A1 | 5/2010 | Jiang et al. | |
| 2012/0059436 A1 | 3/2012 | Fontaine et al. | |
| 2013/0053911 A1 | 2/2013 | Hareland | |
| 2013/0066390 A1 | 3/2013 | Schwibner | |
| 2013/0228485 A1 | 9/2013 | Roach et al. | |
| 2016/0321957 A1 | 11/2016 | Petruzziello | |
| 2016/0328529 A1 | 11/2016 | Kaib et al. | |
| 2017/0157416 A1* | 6/2017 | Medema | A61N 1/3987 |
| 2018/0207435 A1 | 7/2018 | Yetter | |
| 2020/0094044 A1 | 3/2020 | Andrews et al. | |
| 2021/0257849 A1 | 8/2021 | Keil et al. | |
| 2021/0379393 A1 | 12/2021 | Butler | |

* cited by examiner

Fig. 15
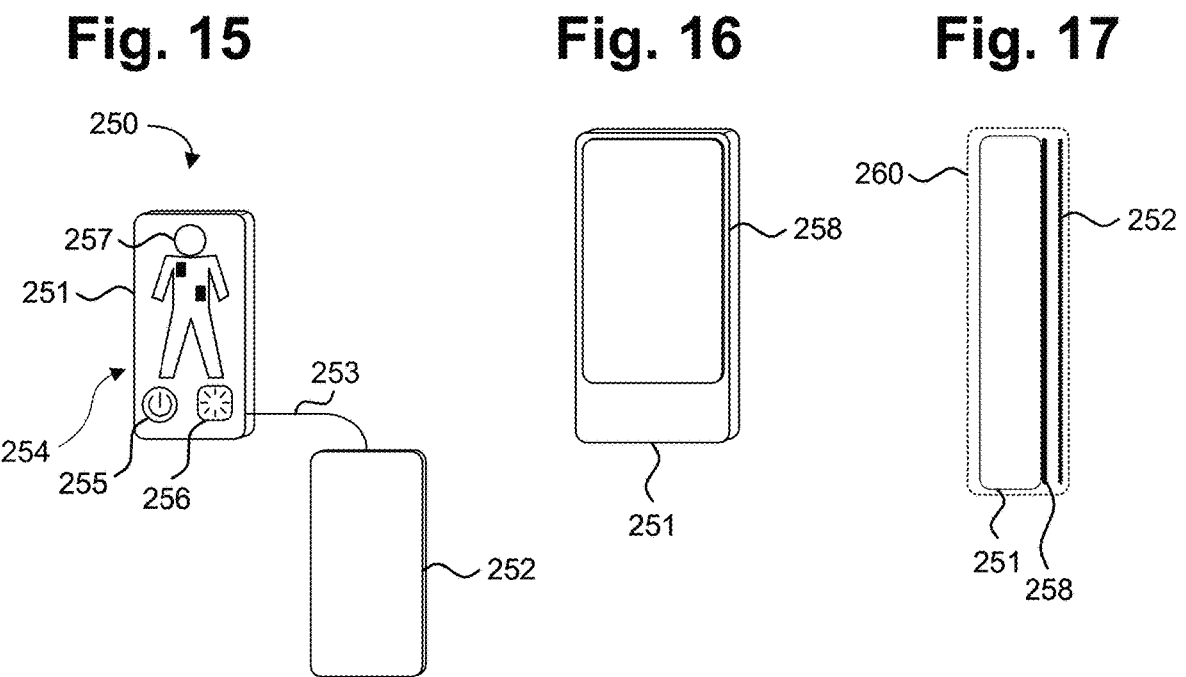
Fig. 16
Fig. 17
Fig. 18
Fig. 19
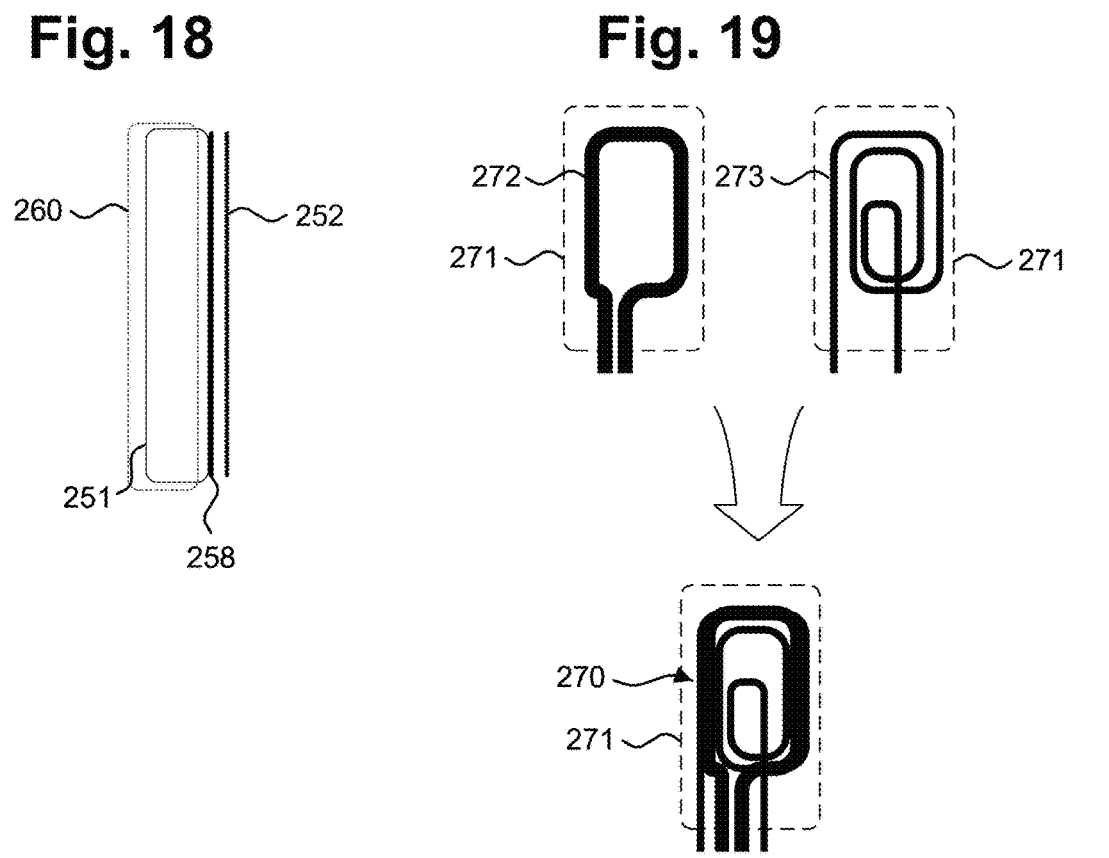

DEFIBRILLATOR

FIELD

This invention relates in general, to circuits for generating defibrillation waveforms and in particular, to a solid-state defibrillation therapy generator that increases AED reliability and decreases AED size.

BACKGROUND

Sudden cardiac arrest (SCA) is a significant cause of mortality throughout the world and remains a major public health concern causing about 300,000 to 450,000 deaths each year in the United States alone, despite the broad scale teaching of cardiopulmonary resuscitation (CPR) and the implementation of public access automated external defibrillators (AED) in hospitals, ambulances and other public locations, like airports and stadiums. More than 9 of 10 SCA victims still die, even in locales with advanced medic response systems. In most rural locations, the death rate approaches 100%.

SCA occurs when the heart suddenly and unexpectedly stops pumping blood, most commonly caused by a chaotic cardiac rhythm disorder known as ventricular fibrillation (VF). VF is a lethal heart rhythm abnormality that causes the ventricles of the heart to quiver ineffectively, resulting in a failure to pump blood. Accordingly, blood pressure plummets and blood delivery to the brain and all bodily organs essential ceases in 5-10 seconds.

SCA from VF constitutes the most time-critical emergency in medicine and is universally lethal within 10-20 minutes without prompt medical attention, specifically the delivery of a high-voltage, high-energy shock across the chest via a defibrillator, the only method known to stop VF. Preferably such a shock is delivered within 5 minutes of the onset of VF.

Victims of VF collapse within 5-10 seconds, lose consciousness, and become unresponsive. Only someone that is physically near the victim has a meaningful chance at preventing death. The chance of survival rapidly decreases 7-10% per minute from onset of VF and, after 10 minutes, resuscitation rarely succeeds, even with CPR, and even if an AED is used, as the heart and brain will have suffered irreversible hypoxic injuries. Consequently, ensuring that people have immediate access to an AED is absolutely essential to saving lives from cardiac arrest, where every minute counts.

AEDs made publicly available, however, have not meaningfully addressed the problem of SCA. By various accounts, there are approximately 3.2 to 4.5 million AEDs currently deployed in public places in the United States, yet an estimated more than 30 million AEDs are needed to provide sufficient coverage to meaningfully improve cardiac arrest survival rate nationally. Moreover, despite this disparity between the number of devices versus the estimated need, increasing the number of public access AEDs by an order of magnitude would be neither practical in terms of cost or execution nor would such an increase address the problem that SCAs primarily occur in places other than where public access AEDs are found. More than 70% of VF cases occur in or near the home or during routine activities of daily living, like yard-work and gardening, driving, personal recreation, and so on, locations where public access AEDs are not usually found. Immediate employment of an AED from time of victim collapse to shock delivery is optimal for survival, yet public access AEDs are rarely deployed or used in locations where SCAs typically happen and, if they are, their use often comes far too late. Thus, the problem of resuscitating victims from VF is inexorably linked to time and proximity to an AED, which are, in turn, inexorably linked to convenience of use, which is a direct consequence of AED cost, size and weight. Accordingly, to make a positive impact of survivability requires a different approach to AED deployment. One solution would be to provide AED devices that are pocket-sized and modest in weight and cost, so that AEDs become practically ubiquitous, similar to a mobile phone.

The high cost and bulk of conventional public access AEDs are mainly due to the design choices of reusability, elimination of all possible failure modes, and telemetry functionality intended to constantly perform and transmit multi-use readiness checks. These typical AEDs perform self-testing constantly, which depletes the battery, and causes wear on the critical components, requiring large and complex circuit designs and components that will survive constant testing and the resulting high voltage bias that is induced. Several AED product recalls have shown this practice to prematurely degrade components, resulting in an AED becoming non-functional when needed. AEDs are typically designed to eliminate failure modes, which, paradoxically, results in large and complex custom components that are expensive and prone to failure. For example, conventional public access AED capacitors are often rated for use at temperatures of 90° C. and 20,000 discharges back-to-back, conditions that do not remotely resemble the typical use case under any conceivable scenario. Moreover, reusability requirements mean that the batteries must be able to store enough energy to defibrillate multiple patients, perform simulated use testing, as well as have a circuit able to sense when there is not enough energy to be "rescue ready" far in the future.

These are key factors that effectively restrict deployment of public access AEDs only to healthcare providers, first responders, and public areas that are legally required to have an AED, all of which make existing AEDs relatively unavailable and of no use for the majority of VF emergencies that occur at or near the home away from public access AEDs. Moreover, public access AEDs are packaged in large carrying cases weighing several pounds that are too bulky to be convenient for ubiquitous use by the public. Furthermore, excluding costs of the perennial replacement of batteries and pads, AEDs typically cost at purchase between $1200 to $3500, which is too expensive for the average person to buy or to serve as an accessory to accompany activities of daily living.

Further, in addition to the bulkiness of the current AEDs and their carrying cases, other components of public access AEDs further limit how small the AED can be made. In particular, typically such AEDs require a use of a transformer for generation of requisite defibrillation and control voltages. In particular, typical AEDs include a transformer with multiple windings that are used to generate bias voltages for high voltage pulse generation circuits. Such transformers tend to be large, usually at least a cubic inch of volume, thus increasing the size of the AED overall because of casing requirements. Further, the use of the transformers requires additional components in the AED that are used to excite the transformer, rectify the transformer's output, and to provide regulation. Such components tend to use high voltages which have rigorous dielectric withstanding requirements and tend to be either bulky or prone to premature failure, especially when such components are miniaturized. This can often limit the lifespan of the AED overall. Further, the possibility of unintended conduction to other AED parts limits how such components can be placed and spaced thereby further increasing size, cost and the risk of malfunction.

Therefore, a need remains for providing a new circuit design for rapidly generating high voltage therapeutic defibrillation waveforms that in turn facilitates the design of low cost and convenient pocket-sized AEDs. Such a design will also decrease the cost and bulk of conventional AEDs and defibrillation circuits in general, be they external or internal defibrillators.

SUMMARY

AED pulse generation circuits that provide floating, adjustable, bias voltages for driving a solid-state defibrillation waveform therapy generator circuit are provided. The provided bias voltages optionally allows to reverse polarity of provided electric shock to increase chances of defibrillation success and survival that can occur in a subset of victims. In one of the provided configurations, unused energy intended for a shock to the patient can be discharged by activating the waveform therapy generator in the transconductance region utilizing a reduced gate voltage. The circuits can be positioned on a self-contained module potted with an insulating material to reduce unintended conductive interactions with other AED components. The use of such circuits reduces the complexity and component count present in traditional AEDs, thus decreasing size and cost of such AEDs while simultaneously improving their reliability.

In one embodiment, a defibrillator is provided. The defibrillator includes: one or more power generation subcircuits configured to generate a variable voltage bias supply; a solid-state defibrillation waveform therapy generator circuit including a plurality of elements at least portion of which is configured to be driven by the variable voltage bias supply, the solid-state defibrillation waveform therapy generator circuit configured to: generate one or more defibrillation waveforms that are conducted to the patient when the variable drive bias voltage is in a high energy state, activating at least some of the elements of the solid-state defibrillation waveform therapy generator in the saturated region; and generate one or more internal discharge waveforms that are isolated from the patient when the variable drive bias voltage is in a low energy state, activating at least some of the elements of the solid-state defibrillation waveform therapy generator in the transconductance region and dissipating energy as heat; and a microcontroller control unit configured to control whether the variable voltage bias supply is provided to the solid-state defibrillation waveform therapy generator circuit at the high energy state or at the low energy state.

In a further embodiment, a defibrillator with multi-level vertical component spacing is provided. The defibrillator includes a module comprising a multi-level configuration, further including a solid-state defibrillation waveform therapy generator positioned on one of the levels of the module and configured to generate therapeutic defibrillation waveforms; and bias generating components positioned on another of the levels of the module and configured to generate bias used for the generation of the therapeutic defibrillation waveforms, wherein the solid-state defibrillation waveform therapy generator and the bias generating components are covered with an insulating material. In a further embodiment, a circuit for defibrillation waveform generation, is provided. The circuit includes a bias generation circuit, including: a switching regulator in buck configuration, wherein switched output of the regulator is connected to an input of a primary winding of a SMPS (switch mode power supply) transformer and wherein an output of the primary winding of the transformer is utilized to supply a regulated DC voltage which powers a microcontroller that is in control of a solid-state therapeutic defibrillation waveform generator; and one or more secondary windings of the transformer whose energy is rectified, wherein the rectified energy is used to supply one or more bias voltages to the solid-state therapeutic defibrillation waveform generator that is used to create a therapeutic defibrillation waveform.

In a still further embodiment, a defibrillator utilizing a therapeutic defibrillation waveform generation circuit is provided. The defibrillator includes a bias generation circuit, including: a switching regulator in buck configuration, wherein the switched output of the regulator is connected to an input of a primary winding input of the transformer, wherein an output of the primary winding of the transformer is utilized to supply a regulated DC voltage to a microcontroller that is in control of a solid-state therapeutic defibrillation waveform generator; one or more of the secondary windings of the transformer whose energy is rectified; and the rectified energy is used to supply one or more bias voltages; and a solid-state defibrillation waveform generator that is configured to create a therapeutic defibrillation waveform utilizing one or more of the bias voltages.

If significantly reducing the number of deaths from SCA due to VF is to be meaningfully addressed, which has been acknowledged as a problem for over 40 years, the design of conventional AEDs must change to lower cost and decrease size and weight, so that AEDs can be ubiquitously made available, including in every home and every car, as well as in many pockets and purses. Thus, by employing the described pulse generation circuits, the size and reliability of an AED can be meaningfully affected, therefore likely yielding an increased survival rate from cardiac arrest by virtue of its ease of availability because of its pocketability and its lower cost that allows large segments of the population to afford its purchase. This technology may also benefit size and cost reductions for wearable and implantable defibrillators as well as fully functional hospital-based defibrillators.

Still other embodiments will become readily apparent to those skilled in the art from the following detailed description, wherein are described embodiments by way of illustrating the best mode contemplated. As will be realized, other and different embodiments are possible and the embodiments' several details are capable of modifications in various obvious respects, all without departing from their spirit and the scope. Accordingly, the drawings and detailed description are to be regarded as illustrative in nature and not as restrictive.

BRIEF DESCRIPTION OF THE DRAWINGS

FIG. 4 is a diagram showing of the pulse generation (discharge) circuit of FIG. 2 in accordance with a further embodiment.

FIG. 15 is a front view showing a disposable single use pocketable AED with a single free-floating electrode in accordance with one embodiment.

FIG. 16 is a rear view showing the integrated electrode of the disposable single use pocketable AED of FIG. 15.

FIG. 17 is a side view showing the disposable single use pocketable AED of FIG. 10 with the housing and single free-floating electrode stowed in a carrying case.

FIG. 18 is a side view showing the disposable single use pocketable AED of FIG. 10 with the housing and single free-floating electrodes partially deployed from the carrying case.

FIG. 19 is a top view diagram showing an electrode pad assembly for use in the disposable single use pocketable AEDs of FIGS. 10 and 15.

DETAILED DESCRIPTION

Figure 1:
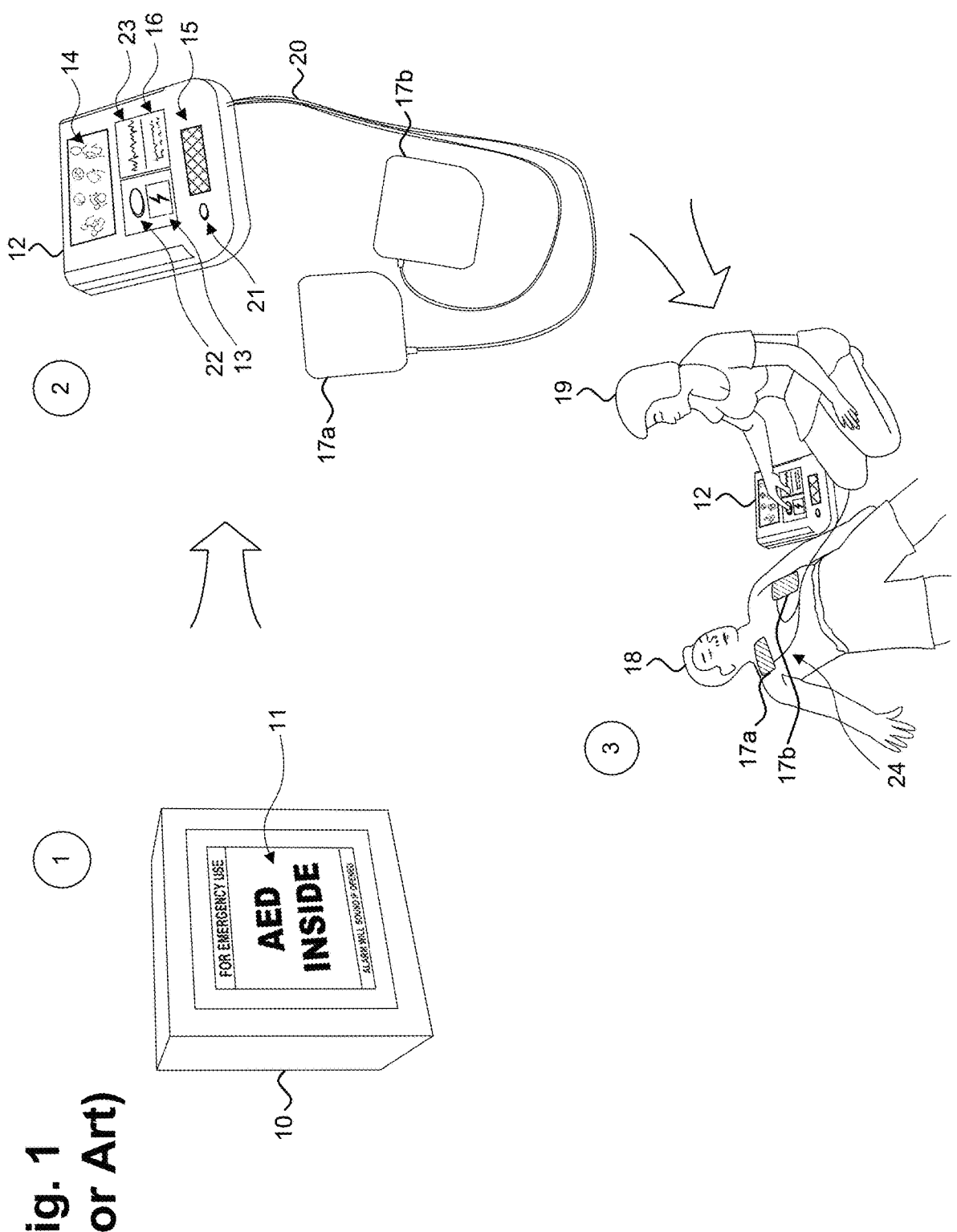
FIG. 1 is a process flow diagram showing, by way of example, a typical prior art use of a public access AED in an SCA situation.

There has been a push to deploy public access AEDs in busy often-frequented places, such as airports, restaurants, casinos, shopping centers, and stadiums. Public access AEDs are relatively easy-to-operate devices for most trained responders that automatically diagnose whether VF (ventricular fibrillation) is present and, if so, urge delivery of defibrillation shocks by a bystander in an attempt to restore normal cardiac rhythm. FIG. 1 is a process flow diagram showing, by way of example, a typical prior art use of a public access AED 12 in an SCA situation. Public access AEDs are designed for repeated use by the general public and require minimal training to operate; users simply follow some combination of voice prompts, text prompts, or both, and diagrammatic instructions to deliver the defibrillation waveforms to SCA victims.

In this example, a victim 18 has suffered suspected cardiac arrest while in the company of a rescuer 19. The terms "victim" and "patient" are used interchangeably and refer to the individual that is receiving emergency care for a possible cardiac arrest. Similarly, the terms "rescuer," "bystander" and "user" are used interchangeably and refer to the individual who is actively providing the emergency care through the use of a public access AED.

When SCA is suspected, often when a victim suddenly loses consciousness and collapses, a rescuer 19 must take immediate action to assist the victim 18, which begins by first locating and obtaining a public use AED 12 (step (1)) and calling 9-1-1. Note that there are two main categories of AEDs, either of which may be found in use as a public use AED. Some AEDs automatically deliver shocks without rescuer action when VF is detected. Most AEDs are semi-automatic and require the rescuer to manually trigger a shock with a button or device control. The portable AEDs carried by emergency medical services (EMS) personnel are generally designed as semi-automatic AEDs that include physiological monitoring tools for both basic and advanced life support, as well as vital signs patient monitoring.

A typical public access AED 12 is located where the general public ordinarily has access kept in some type of protective housing 10, such as a display case, wall cabinet or kiosk. Public access AEDs are designed for long-term reuse and to be available to save multiple victims over their service lifetime, factors that add to unit cost and size, including maintenance obligations and telemetry functionality needed to prevent failures and sustain readiness over time. The public access AED 12 itself is portable and therefore susceptible to being misplaced or stolen; the protective housing 11 helps to keep the public access AED 12 secure and available until needed. Note that, despite being portable, a public access AED kit is bulky and weighs several pounds, which makes carrying a public access-type AED on an everyday basis impractical for most people, even though wider AED availability and use could help save more lives. In addition, both the electrodes and batteries of public access AEDs have expiration dates and must be replaced upon their respective expiry every one to three years. Moreover, these AEDs must undergo periodic operational testing that may require that the defibrillation circuit be energized, resulting in further depleting the battery and prematurely degrading the circuit.

Returning to the steps of AED use in public, once the rescuer 19 locates and obtains an AED, the rescuer must activate the AED 12, which generally entails pressing an "On" button or other controls (step (2)). Conventional public use AEDs 12 are packaged in a large carrying case that contains the AED circuit, including sensing and defibrillation circuit and battery, a pair of adhesive dermal electrode pads 17*a-b* connected by a set of leads 20, and support accessories (not shown), such as gloves and a face shield. Electrode pads are generally about 8-12 cm in length, rectangular, and intended to conform to the human thoracic anatomy.

As some rescuers will be lay bystanders, public use AEDs generally provide visual instructions 14 on assessing the victim's breathing and placement of its electrode pads 17*a-b* on the victim's chest 24 (step (3)). A note should be made however that many public rescuers are in fact medical personnel who take the initiative as a Good Samaritan. Nevertheless, the AED includes a set of necessarily simple controls, typically an "On" button 21 and, if the AED is semi-automatic, a "Shock" button 22 to manually deliver a defibrillation shock by the rescuer, plus a warning indicator 13 that the AED is charged and ready to deliver a defibrillation shock. To activate the public use AED 12, the rescuer 19 simply presses the "On" button 21. The visual instructions 14 are typically supplemented with speaker-generated voice prompts 15, display-generated text prompts 16, in some cases, an electrocardiogram (ECG) 23, or some combination of voice prompts, text prompts and an ECG. The American Heart Association (AHA) and European Resuscitation Counsel (ERC) publishes guidelines outlining a recommended but not mandatory sequence of visual and voice prompts to help rescuers in proper use of AEDs. See, 2010 *American Heart Association Guidelines for CPR and ECC*; Supplement to *Circulation*, Vol. 192, Issue 18 (Nov. 12, 2010). *European Resuscitation Council Guidelines for Resuscitation* 2010, *Resuscitation* Volume 81 (October 2010).

The paddles or electrode pads 17*a-b* must be applied by the rescuer 19 to be in direct contact with the victim's skin. Electrode pads are typically adhesive and, in many AED kits, a razor is included to shave hair off the victim's skin, if needed, on the anatomy where electrode pads are to be placed. To maximize the transit of current through the heart, an anterior-lateral position for electrode pad placement on the victim's chest 24 is preferred. The anterior pad is applied on the right anterior upper chest 24 just below the right clavicle. The lateral pad is applied immediately below and lateral to the left nipple. In female patients, the lateral pad should be applied on the chest wall below and lateral to the left breast, and not over the breast tissue.

With the pads in place, the typical traditionally AED commonly in use will determine if a shockable rhythm is present depending upon the ECG obtained from the pads and instruct the rescuer to deliver a defibrillation shock, if required, to stop VF and allow the heart to reestablish an effective normal rhythm. If the public use AED 12 is semi-automatic, the rescuer 19 will need to manually administer the shock by pressing the "Shock" button 22. At times, traditionally, multiple shocks may be required whereupon rhythm analysis by the AED (step (4)) dictates the timing of recurrent defibrillation shocks. Resuscitation of the victim 18 is unlikely if defibrillation is unsuccessful and/or is delivered too late. Some AEDs provide for escalating energy delivery when a previous shock attempt fails to terminate VF as determined by the ECG. Higher energy delivery may or may not restart the heart, but also more likely to cause temporary damage to cardiac tissue. Further, AEDs with higher shock energies also result in increased weight and cost of the AED minimizing its portability and broad availability and have been well demonstrated to not be required in the early rescue process to terminate ventricular fibrillation.

Moreover, public access AEDs are designed and built to save multiple victims over the service life of the device despite long periods of idle standby storage. These requirements lead to a complex, large, and typically over-engineered design, which also leads to high cost and long-term maintenance obligations. The design and construction of public use AEDs uses large heavy batteries and costly electronic components intended to ensure operability when and if the AED is needed for use. And yet, such costly designs often fail because of their complexity.

As public use AEDs are big and bulky, they are ordinarily only going to be found in a stationary place in a controlled access protective housing, which inherently limits their availability during a SCA emergency and, to a large extent, renders public use AEDs largely ineffective in reducing the number of deaths caused by most SCA deaths that occur in the private settings of the home. Public use-type AEDs are also expensive and seldom found outside of areas where their placement is legally required given the significant economic burden associated with both initial acquisition and ongoing maintenance costs that often exceed the initial price of the AED. Thus, even though most SCAs occur in the home, AEDs are seldom found there, or in countless other random places where people often suffer a SCA, such as in cars and private boats, in parks or trails where people are walking, exercising or enjoying the outdoors, and where people are visiting with friends, and so forth. Despite being portable, the size and weight of a full public use AED kit makes carrying one personally in a backpack or stowed in the glove box of a car impractical.

Conventional AEDs are battery powered and include a charging circuit that uses a step-up transformer to increase battery voltage from low voltage in the range of 6-24 volts (V) to around 1000-6000 V (note that higher voltages are rarely used today), a rectification circuit to convert the high voltage AC energy from the step-up transformer to direct current (DC) energy, and a pulse capacitor to store the energy prior to defibrillation shock delivery. These traditional pulse capacitors are rated to handle high voltage and large sudden discharge currents; as a result, they can be difficult to manufacture and are prone to failure, thereby increasing associated costs. Once this type of legacy pulse capacitor is charged, the AED is ready to deliver a defibrillation shock and the charging circuit switches the energy to the patient, whereby the current is delivered to the victim's chest to complete the circuit. For successful defibrillation, the current delivery waveform must be physiologically appropriate.

Current commercially available AEDs generally employ biphasic truncated exponential (BTE), pulsed biphasic, or rectilinear biphasic waveforms. In contrast to the historical use of monophasic waveforms, properly designed biphasic waveforms are both more effective and require less energy for defibrillation. Accordingly, monophasic waveforms are no longer used. With a biphasic defibrillator, the initial energy level for defibrillation typically begins at 120 J (although it can be less) and can escalate for the second and subsequent defibrillation shocks up to a maximum of 360 J. Energy choice and escalation are waveform- and manufacturer-specific.

This historical background of the status quo notwithstanding, the life-saving benefits of AEDs can be more efficaciously provided to every person, everywhere and on a 24/7/365 basis through a disposable, single-use AED that is small enough to be truly portable, for instance by fitting in an average-sized pocket. A single use AED, that is, a device that is available to therapeutically treat one instance of SCA, significantly streamlines and simplifies the design requirements of the AED and accordingly makes it possible to house the AED in a small pocketable form factor. Periodic maintenance is not required, as the disposable nature of the pocket AED implies the device will be discarded before needing to undergo maintenance or other testing prior to use on a patient. As well, the failure ratings of the electronic components need only accommodate one use, rather than repeated uses over an extended service life of many years, limiting complexity and improving durability. Similarly, the battery can be smaller and lighter, as battery life will not be depleted by long shelf life and telemetry transmissions related to diagnostic routines and maintenance test cycles.

Further, the use of such simplified electronic components and battery technologies lowers cost and allows disposability to be realized. Finally, to encourage being carried by users at all times, the pocket AED is sized comparably to a conventional smartphone, for instance, in the range of 2.25 to 3.5 inches wide, 5.25 to 7 inches long, and 0.25 to 1.5 inches thick, and of similar weight, for example, in the range of 130 to 550 grams.

Figure 2:
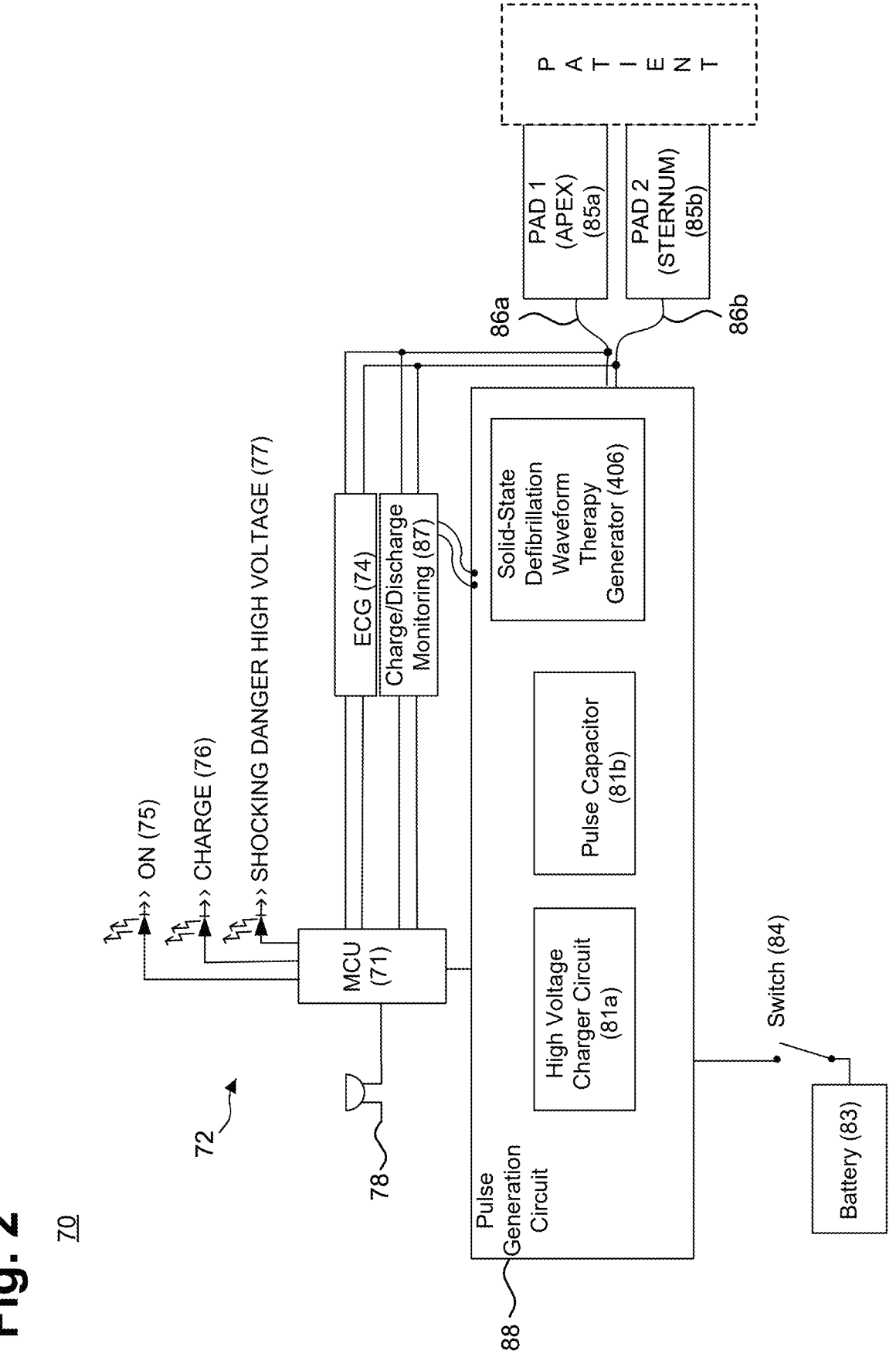
FIG. 2 is a block diagram showing functional components and a user interface for a disposable single use pocketable AED in accordance with one embodiment.

To facilitate the construction of a disposable pocketable AED to fit into a small form factor, various charging configurations are provided. FIG. 2 is a block diagram showing functional components and a user interface 72 for a disposable pocketable AED. For the sake of clarity, only the defibrillation circuit 70 will be discussed in detail.

The defibrillation circuit 70 includes components for providing a basic user interface 72 that includes an "On" switch (not shown), a "Power On Indicator" 75, a charging indicator 76, and optionally, a warning indicator 77 that indicates defibrillation shock delivery readiness with attendant dangers of exposure to high voltage, plus an optional speaker 78 through which audible instructions can be played. The user interface 72 also includes a visual display (not shown) on which text prompts can be displayed. In one embodiment, an AED incorporating the defibrillation circuit 70 can be semi-automatic and require the rescuer to manually trigger a shock by actuating the charging indicator 76; in a further embodiment, an AED incorporating the defibrillation circuit 70 employs a circuit to automatically deliver the defibrillation shock to the victim without user action once the pulse generation circuit 88 is ready, that is, the pulse capacitor 81b is charged by a high voltage charger circuit 81a and is ready to provide power to a solid-state defibrillation waveform therapy generator 406, and after the user has been warned to avoid any direct physical contact with the patient during shock delivery.

The defibrillation circuit 70 is controlled by a microcontroller unit (MCU) 71 or system-on-chip controller (SoC) (not shown) that is micro programmable, which allows updated controller firmware to be downloaded from an external programmer into a persistent memory store. Sensing circuit 87 is connected in line with the inputs and outputs of a discharge and polarity control circuit 82. The sensing circuit 87 determines whether a shockable rhythm is present and monitors for the MCU 71 the defibrillation energy that is received from the pulse capacitor 81b as an input to the discharge and polarity control circuit 82 and the defibrillation waveform or "pulse" that is output. ECG front end circuit 74 evaluates heart rhythm for the MCU 71. The ECG front end circuit 74 taps off the leads 86a-b of the pair of electrode pads 85a-b to sense cardiac signals, while the sensing circuit 87 taps off the discharge and polarity control module's input leads to monitor the shock delivery process. The sensing circuit 87 is implemented through conventional VF detection algorithms to detect the presence of a shockable rhythm, such as published by A. Fan, et al., Shockable Rhythm Detection Algorithms for Electrocardiogram in Automated Defibrillators, AASRI Conf. on Comp. Intel. and Bioinfor. pp. 21-26 (2012). The ECG front end circuit 74 is implemented through conventional heart function evaluation algorithms, such as provided through the ADS1x9xECG-FE family of integrated analog front-end ECG circuits, available from Texas Instruments, Dallas, TX. Other types and configurations of sensing and ECG front end circuitries are possible.

When a shockable rhythm is detected, based on inputs from the sensing circuit 87 and the ECG front end circuit 74, the MCU 71 determines the parameters of a defibrillation waveform in terms of energy, voltage, and pulse width; the defibrillation waveform is algorithmically selected based on the nature of the shockable rhythm to be medically appropriate for restoring normal cardiac rhythm. Up to a maximum of three shocks may be needed if the victim fails to be resuscitated, after which further shocks are generally futile.

In response to the sensing circuit 87 determining that a shockable rhythm is still present after initial shock delivery, that is, defibrillation failed to establish normal cardiac rhythm, the MCU 71 may simply repeat the delivery of the defibrillation pulse or, if appropriate, revise the parameters of the defibrillation waveforms for the subsequent pulses. In this situation, subsequent defibrillation shocks may need to be escalated for the second and subsequent defibrillation shocks, generally up to a maximum of 360 J. In a further embodiment, parameters consisting of one or more of energy, voltage and pulse width are adjusted by the MCU 71 in real time, as further discussed infra with reference to FIG. 9.

Figure 3:
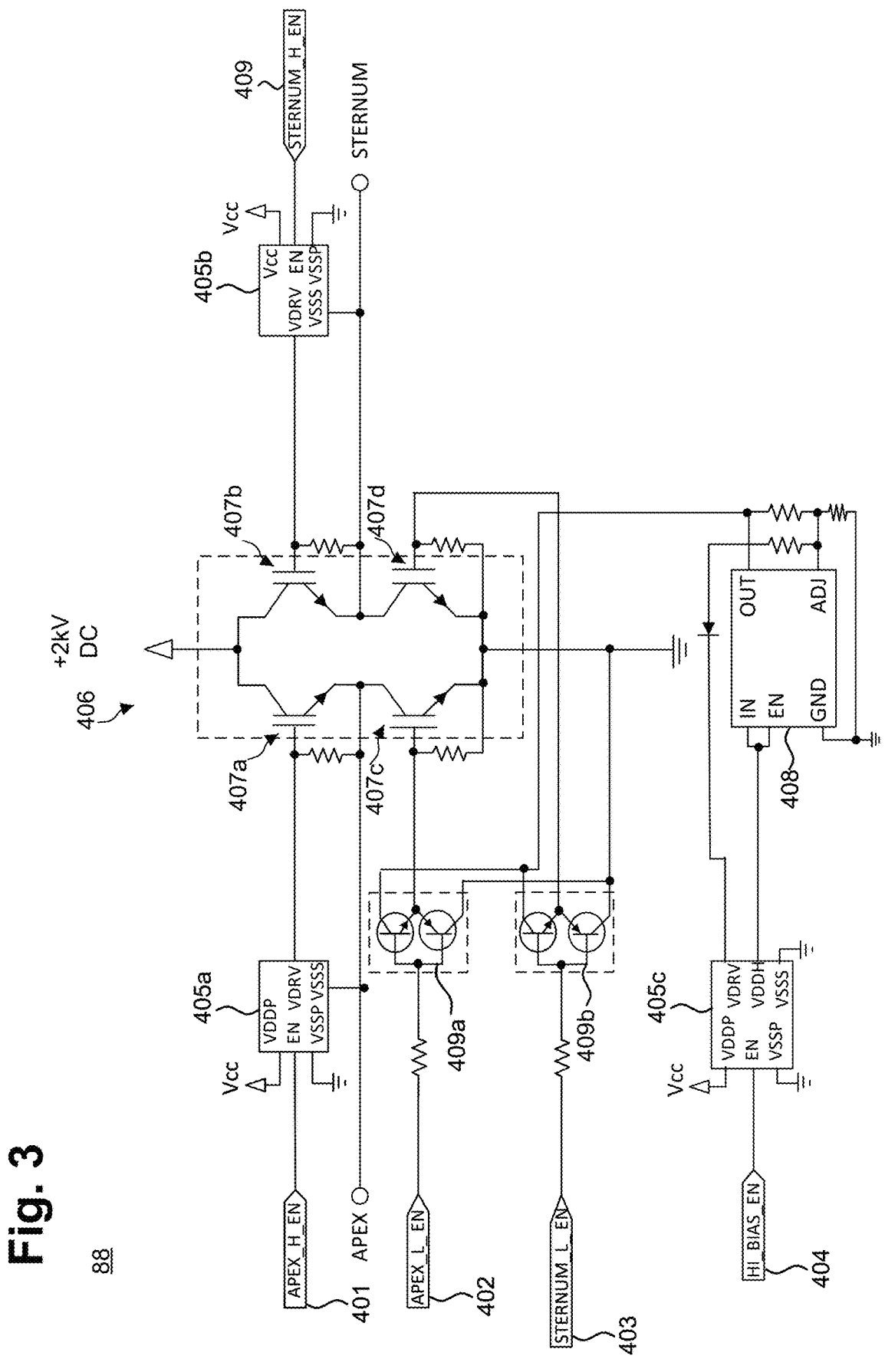
FIG. 3 is a diagram showing of the pulse generation (discharge circuit) of FIG. 2 in accordance with one embodiment.

Defibrillation energy is generated and stored as part of a pulse generation circuit 88 (also referred to as a waveform generator 88) that includes multiple power generation sub-circuits. FIG. 3 is a diagram showing Waveform Generator 88 88 of FIG. 2 in accordance with one embodiment. The power generation sub-circuits 405a-b provide a floating bias voltage where 405c provides a floating, adjustable voltage that is used as a bias supply for a solid-state defibrillation waveform therapy generator circuit 406 that generates the defibrillation shock provided to the patient through the pads 85a, 85b (also referred to as electrodes 85a, 85b). In particular, the solid-state defibrillation waveform therapy generator circuit 406 includes multiple solid-state switching elements 407a-d whose output, when combined, determines the polarity of the defibrillation waveforms delivering the shock. In one embodiment, the solid-state defibrillation waveform therapy generator 406 can be in the form of an H-Bridge while the elements 407a-d can be one or more of a field-effect transistors (FETs), and one or more silicon-controlled rectifiers (SCRs), triode for alternating current (TRIAC), a bipolar junction transistors (BJTs) or a combination of one or more of the different types of elements 407a-d. The components with an insulated gate can in turn can include one or more insulated-gate bipolar transistors (IGBTs) one or more Silicon Carbide FETs, though other types of FETs are also possible. Still other types of elements 407a-d are possible. In one embodiment, the solid-state defibrillation waveform therapy generator circuit 406 can be MMIX4B22N30 High Voltage, High Gain BIMOSFET™ Monolithic Bipolar MOS Transistor sold by IXYS Corporation of Milpitas, California, though other types of the solid-state defibrillation waveform therapy generator 406 switching components 407a-d are also possible.

As further described below, the polarity of the defibrillation shock delivered by the solid-state defibrillation waveform therapy generator 406 can be inverted through controlling the floating, optionally adjustable voltage that is delivered to each of the solid-state switching elements 407a-d. By controlling which of the elements 407a-d are open and closed during the delivery of a particular shock, individually or in unison, the polarity of the shock (i.e. which of the electrodes 85a, 85b as the anode during the delivery of the shock) is also controlled.

The power generation sub-circuits 405a-c are electrically isolated from each other and provide both the free floating, bias voltage and control signals to the elements 407a-d. In particular, each sub-circuit 405a-c includes at least two domains that are separated by one or more isolation barriers, with each domain having a bias voltage ground reference that is independent of the ground reference in the other domain and the ground references between the domains being different. The sub-circuits 405*a-c* receives energy (also referred to as power in the description below) from the battery 83 and control signals from the MCU 71 via the pins 401, 402, 403 and 409 respectively in one of the domains, and pass the control signals and the power through the one or more isolation barriers from one domain to another domain. The power and control signals can be transmitted through the one or more isolation barriers in a variety of ways, such as by modulating power transmission and the control signals through an isolated power transmission circuit, by utilizing alternating magnetic fields, by utilizing capacitive coupling, by utilizing optical coupling, by utilizing radiofrequency (RF) coupling, or a combination of one or more of these techniques. Still other ways to transmit the power and control signals through the one or more isolation barriers are also possible. The pin 404 is used to control the bias voltage of switching components 407*c* and 407*d*. When driven low, a regulator (408) decreases the floating bias voltage resulting in elements 407*c* and 407*d* operating in a high resistance transconductance region. When operating in this region, the residual energy stored in the pulse capacitor 81*b* may be safely shunted internally by activating elements 407*a* and 407*c* or elements 407*b* and 407*d*.

By passing through the one or more isolation barriers, the power received from the battery 83 (via the switch 84) is coupled through charge injection to achieve the free floating, adjustable bias voltage that can be used for driving one (or two in the case of the sub-circuit 405*c*) of the solid-state switching elements 407. In one embodiment, the sub-circuits 405*a-c* can be TPSI3052 Isolated Switch Driver with Integrated 15-V Gate Supply sold by Texas Instruments Incorporated of Dallas, Texas, though other kinds of sub-circuits 405*a-c* are possible. For example, the sub-circuits 405*a-c* can be AHV85110 "Self-Powered Single-Channel Isolated GaN FET Gate Driver with Power-Thru Integrated Isolated Bias Supply" distributed by Allegro Microsystems of Manchester, NH, though other kinds of sub-circuits 405*a-c* are also possible.

The sub-circuits 405*a* drives only the element 407*a* and the sub-circuit 405*b* drives only the element 407*b* due to the elements 407*a-b* being interfaced to the patient through one of the electrodes 85*a*, 85*b* and thus requiring separate ground references. However, the elements 407*c* and 407*d* can share a common ground reference; these elements, 407*a*, *b*, are provided a reference by only a single sub-circuit 405*c*, allowing to reduce space required by the charge circuit 88.

The bias voltage generated by the sub-circuit 405*c* is in turn regulated by a linear regulator 408 as low voltage may be required to operate ports of the waveform generator 406 in the transconductance region. In one embodiment, the linear regulator 408 can be NCV8730ASNADJT1G linear regulator sold by Semiconductor Components Industries, LLC dba ONSEMI of Scottsdale Arizona, though other linear regulators are also possible. The linear regulator 408 is in turn interfaced to two gate drivers 409*a*, 409*b*. The gate driver 409*a* is interfaced to the pin 402 and provides the regulated bias voltage or ground to the element 407*c*. The gate driver 409*b* is interfaced to the pin 403 and provides the regulated voltage to the element 407*d*. Through the gate drivers 409*a*, *b*, the sub-circuit 405*c* can drive the elements 407*c* and 407*d* independently of each other.

The use of the independent, isolated sub-circuits 405*a-c* to independently generate a bias voltage for the elements 407*a-d* avoids including a bias generation transformer as part of the pulse generation circuit 88, thus allowing a decrease in the size and an increase in the reliability of the AED overall. Further, the use of the independent, isolated sub-circuits 405*a-c* allows the power generation circuitry to be distributed in advantageous locations simplifying routing of the AED. When energy is stored in the pulse capacitor of the pulse capacitor (81*b*), but the energy is not delivered (for example spontaneous restart of the heart's normal rhythm), the energy stored in the capacitor needs to be discharged safely. Conventionally, such stored energy is discharged through a dedicated discharge circuit consisting of a resistor, inductor or resistor with an inductor in series, which adds volume, weight and cost to the AED while greatly reducing reliability. The pulse generation circuit 88 of FIG. 3 is able to discharge the stored energy without a dedicated discharge circuit by activating the solid-state defibrillation waveform therapy generator 406 elements 407*a* and 407*c* or element 407*b* and 407*d* in the transconductance region. The activation in the transconductance region allows the solid-state defibrillation waveform therapy generator 406 to safely transform the power absorbed by the switching elements 407*c* and 407*d* into heat and thus safely discharge the energy stored in the pulse capacitor 81*b* initially charged for delivering the defibrillation shock that is no longer needed because of spontaneous restoration of a normal cardiac rhythm. Other reasons for which the discharge of the pulse capacitor 81*b* may be needed can include: the defibrillator being off; the defibrillator running out of battery and not being able complete another shock (with making a prediction regarding sufficient power being in the battery not being possible to predict in certain circumstances before charging the capacitor); the defibrillator having an irrecoverable failure; a defibrillator malfunction being detected; an unsafe leakage current being detected; patient safety reasons; service reasons; the capacitor having been charged for too long; and the shock being aborted for any reason, though still other reasons are possible. When discharging the energy, the gate voltage at which the power is provided to the solid-state defibrillation waveform therapy generator 406 is lower than the voltage at which the power is provided to the generator 406 for generating the defibrillation shock to reduce the amount of heat that is generated over a period of time (by running the h-bridge 406 in the saturated region). The reduction in the voltage is accomplished using the voltage regulator (408) controlled by the isolated driver portion of subcircuit 405*c*. In one embodiment, all pairs of elements 407*a-d* of the generator 407 could be activated sequentially one or more times to discharge the prepared energy through heat. For example, at first the elements 407*a* and 407*c* could be activated at the same time, and then after a pause to allow the generated heat to dissipate, the elements 407*b* and 407*d* could be generated one after another, with a pause being made between the activations to allow the generated heat to dissipate. Other sequences of activation are also possible. While the waveform generator 88 is operated in the transconductance region, the MCU 71 controls the waveform generator 88 to shunt energy provided to the generator 88.

Figure 4:
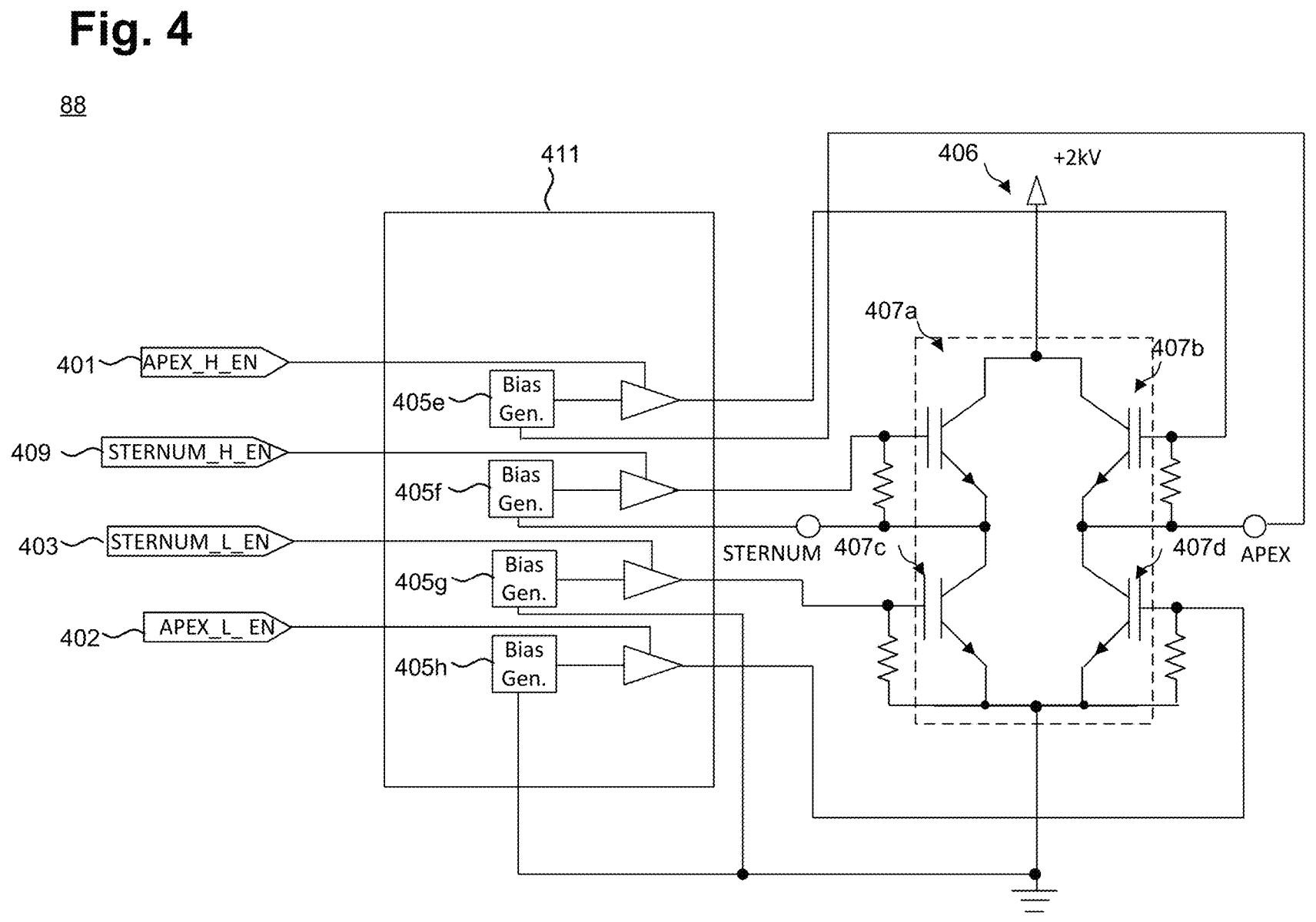

In a further embodiment, the functionality of the sub-circuits 405*a-c* could be integrated into a single circuit. FIG. 4 is a diagram showing of the pulse generation circuit 88 of FIG. 2 in accordance with a further embodiment. In the embodiment accordingly shown with reference to FIG. 4, four sub-circuits 405*e-h* that are structurally and functionally equivalent to the sub-circuits 405*a-c* of FIG. 3 are integrated into a single circuit 411 that is connected to the four pins 401-403, 409 and that provides the free floating, adjustable bias voltage and control signals that drive the solid-state switching elements 407a-d of the solid-state defibrillation waveform therapy generator 406 in the same way as described above with reference to FIG. 3. The solid-state defibrillation waveform therapy generator 406 and the elements 407a-d can be the same as described above with reference to FIG. 3. As generating the low voltage necessary for activating the solid-state defibrillation waveform therapy generator 406 in the transconductance region, a custom ASIC may be employed for an integrated solution, or the output voltages of 405e-h may be downregulated through the use of a linear regulator or other voltage reducing circuit. The pulse generation circuit 88 in the embodiment of FIG. 4 may optionally include a dedicated discharge circuit (not shown) that is interfaced to the pulse capacitor (81b) and that includes a resistor through which energy accumulated for delivering a defibrillation shock that was not delivered to the patient can be discharged.

Figure 5:
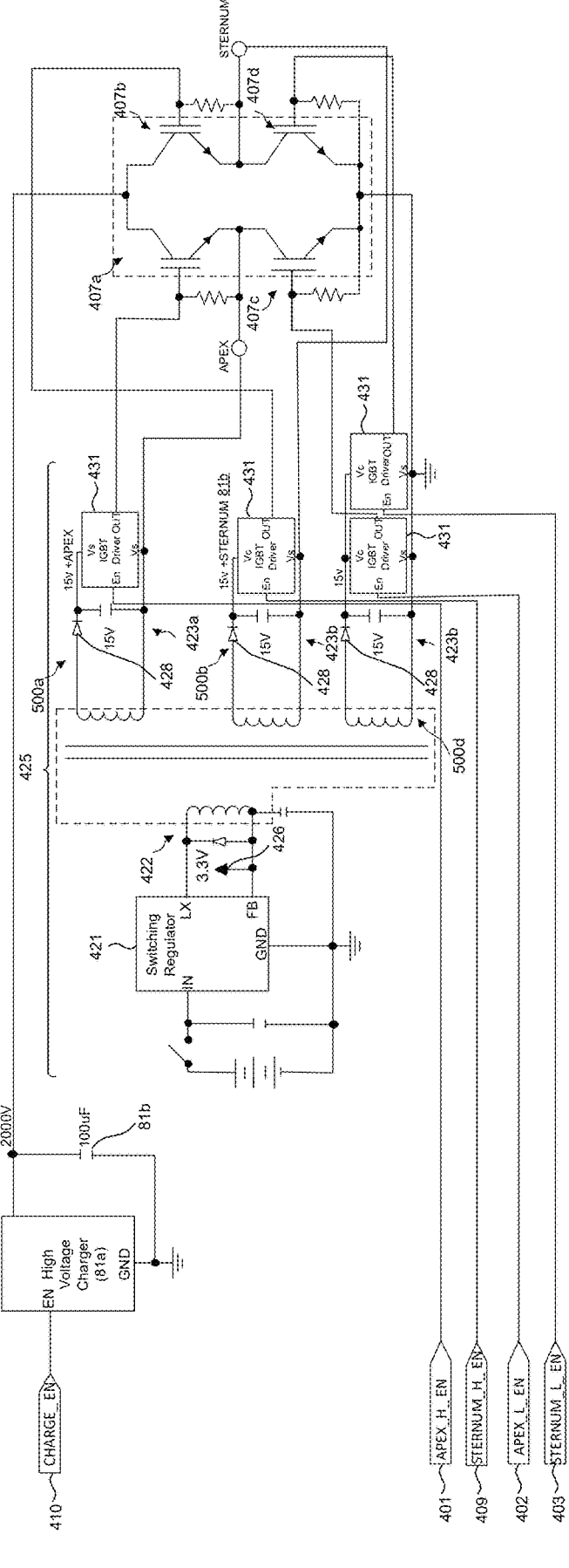
FIG. 5 is a diagram showing the pulse generation (discharge) circuit of FIG. 2 as well as portions of the charging circuit providing power to the MCU in accordance with a still further embodiment in which a buck fly configuration is utilized to provide power to the low-voltage digital electronics such as the MCU.

In a still further embodiment, the pulse generation circuit 88 can utilize a buck-fly topology for generation of multiple bias voltages that drive the solid-state defibrillation waveform therapy generator 406. FIG. 5 is a diagram showing of the pulse generation circuit 88 of FIG. 2 in accordance with a still further embodiment in which a buck-fly configuration is utilized. In the embodiment shown with reference to FIG. 5, the pulse generation circuit 88 includes a switching regulator 421 in buck configuration. In one embodiment, the switching regulator 421 can be a switching controller with an integrated switching element, or a switching controller with an external switching device such as a FET, though other kinds of switching regulators are also possible. The switching regulator 421 is interfaced to a transformer 425 that has a primary winding 422 and one or more secondary windings 423a-c.

The switching regulator 421 is connected to an input of a primary winding 422 and the switched output of the switching regulator 421 is provided to the input of the primary winding 422. The primary winding 422 acts as an inductor in a DC-DC convertor configuration. Secondary isolated voltages are scavenged by secondary bias windings 500a, 500b, 500c. During off time, the input of the primary winding 422 is protected by an element such as a freewheeling diode 426 (or alternatively by using a regulator that features a synchronous rectifier) that provides a current return path that keeps the voltage on the primary winding from 421 going too high when LX (switch pin of the switching regulator 411) is an open circuit (presuming the switching regulator chosen is not of the synchronous type). Further, the output of the primary winding 421 is utilized to supply a regulated DC voltage which powers the low-voltage digital circuitry such as the MCU 71 controlling the solid-state therapeutic defibrillation waveform generator 406 and optionally other parts of the AED.

The transformer 425 is a step-up transformer and there is an increase in the voltage between the primary and secondary windings 423a-c. The output of the transformer 425 is also provided through the secondary windings 423a-c that is rectified and then used to drive the elements 407a-d of the solid-state defibrillation waveform therapy generator 406.

Before reaching the elements 407a-d, the output of the secondary windings 423a-c is converted to a DC voltage by a rectifier. The rectifier can be a rectifier diode 428, a bridge rectifier, or a synchronous rectifier, though other kinds of a rectifiers are also possible. Further, after passing through the rectifier, the bias voltages from each of the secondary windings 423a-c passes through one or more drivers 431 that switch the bias voltage and in turn each deliver the switches bias voltage to one of the elements 407a-d. The four pre-drivers include two high-side pre-drivers and two low-side pre-drivers, with the four pre-drivers driving the four elements 407a-d of the waveform generator 406. Similarly to what is described above, by individually actuating the elements 407a-d, the polarity of the waveforms delivered by the waveform generator 406 can be reversed under control of the MCU 71 if previously delivered shocks of opposite polarity do not achieve termination of the victim's ventricular fibrillation. While the drivers 431 are referred to as IGBT drivers 431 with reference to FIG. 5, when the elements 407a-d are other than IGBTs, the drivers 431 would correspondingly be drivers of the other kinds of elements 407a-d. The drivers 431 are in turn connected via pins 401-403, 409 through which they receive control signals and power from the MCU 71 and the battery 83 (via the switch 84) respectively. FIG. 5 also shows the high voltage charger circuit 81a charging the pulse capacitor 81b, with the pulse capacitor 81b in turn supplying the energy to the waveform generator 406. The charger circuit 81a is connected to the MCU 71 by the pin 410 to receive an enable signal. While the charger circuit 81a and the pulse capacitor 81b are not shown with reference to FIGS. 3 and 4, they can be used for charging the waveform generator 406 shown in the embodiments of the FIGS. 3 and 4 in the same way and with the charger circuit 410 being connected to the pin 410 in the same way.

Figure 6:
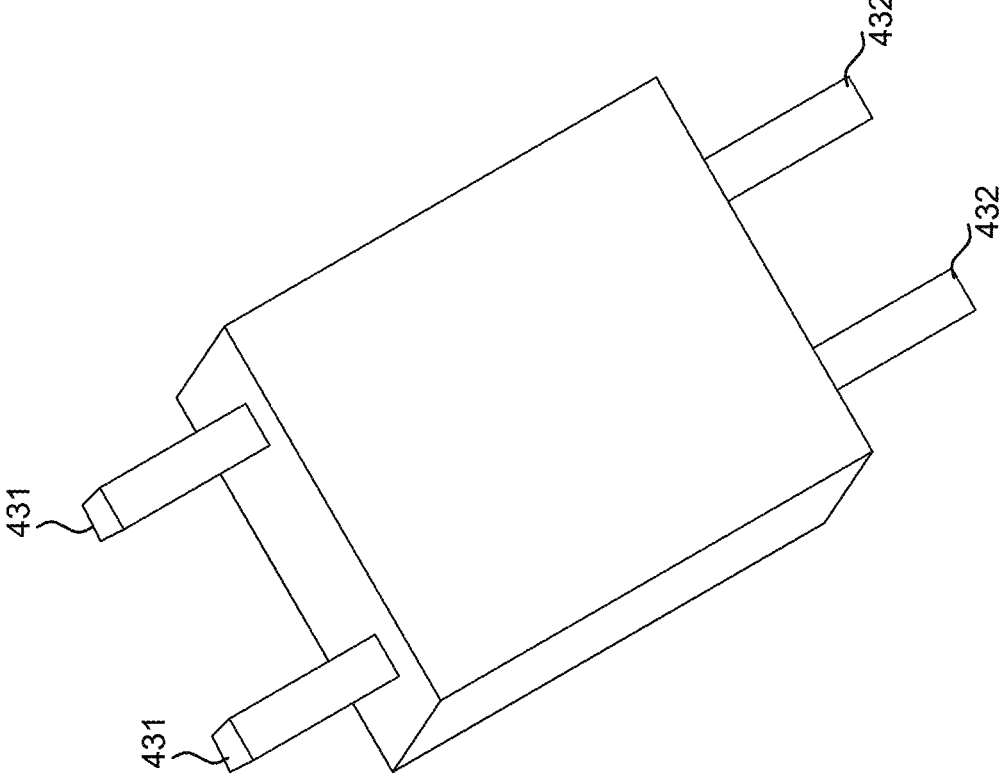
FIG. 6 is a perspective view of an isolated module that includes the pulse generation circuit for use in the AED of FIG. 2 in accordance to one embodiment.

Conventionally, integrating high-powered components such as the pulse generation circuit 88 described with reference to FIGS. 3-5 into an AED requires consideration of dielectric spacing to prevent conducting between components that are not intended to interact with each other. Thus, significant spacing has to be provided between the high-powered components and other components of the AED, thereby increasing the AED size. This challenge can be addressed by including the pulse generation circuit 88 described above with reference to FIGS. 3-5 (as well as optionally other components of the AED) in a self-contained module that includes connections to power, control signals, and electrodes 85a, 85b connected to a patient receiving defibrillation therapy and that is potted inside with an insulating material. FIG. 6 is a perspective view of an isolated module 430 that includes the pulse generation circuit 88 for use in the AED of FIG. 2 in accordance to one embodiment. The pulse generation circuit 88 of any of the embodiments of the FIGS. 3-5 is at least partially enclosed within the module 430 that is filled with an insulating material that enhances dielectric properties. Any parts of the circuit 88 that are not within the module 430 can be similarly covered with the insulating material. The insulating material can be epoxy, acrylic, cured silicone, silicone coating, parylene, or another insulating material, and can be applied to the printed circuit board within the module such as through using vacuum, spray or pouring although other techniques are also possible. Underneath the insulating material, the circuit board additionally can be coated with a dielectric insulating material such as parylene, acrylic, silicone or another insulating coating. Once the insulating material has been applied, the conventional spacing rules can be reduced as undesired electrical interactions between the components on the module 430 or the components on the module 430 and other parts of the AED is inhibited by the improved dielectric properties of the insulating materials. The module 430 further includes electrical connections 432 that will interface to the patient through the electrodes 85a, 85*b*, and electrical connections to pulse capacitor 81*b*. Auxiliary connections (436) connect the module 430 to the battery and the MCU 71.

Figure 7:
FIG. 7 is a view of a top surface of the module of FIG. 6 in accordance with one embodiment.
Figure 7:
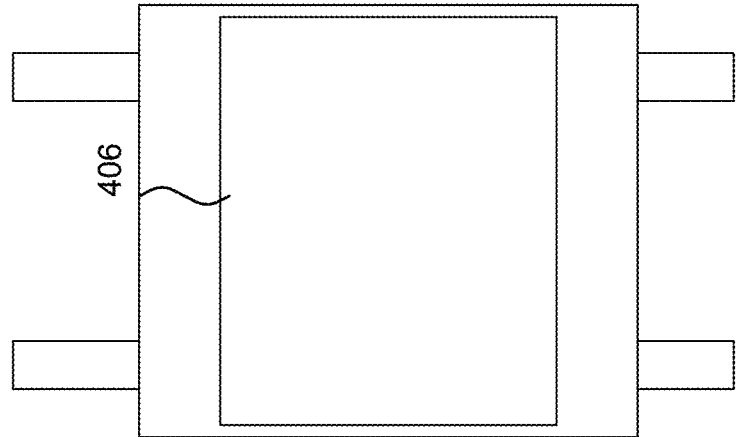
Figure 8:
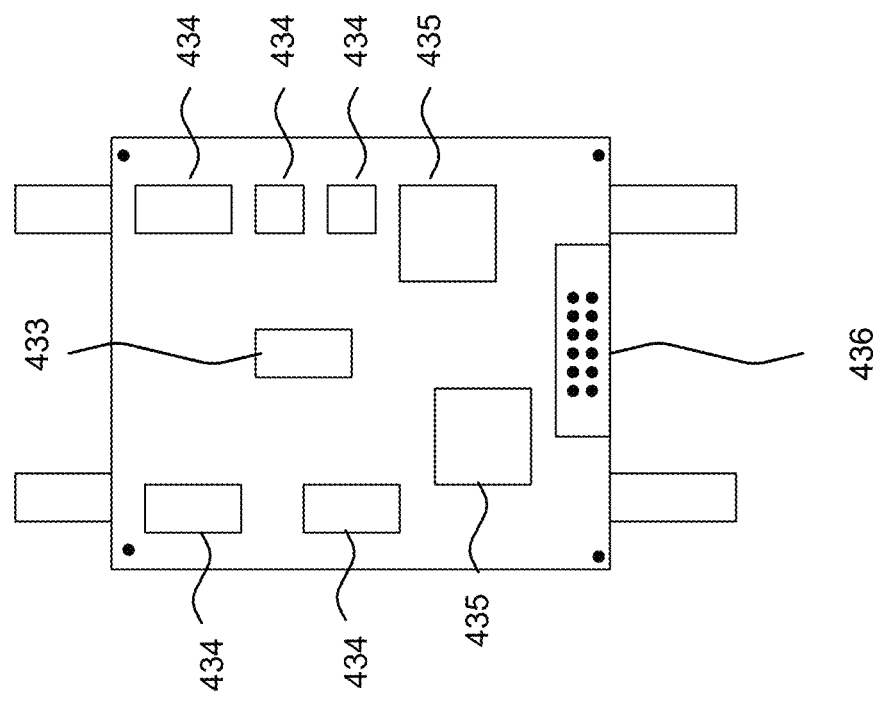
FIG. 8 is a bottom of the module of FIG. 6 in accordance with one embodiment.

Due to the applied insulating material, other components can also be positioned on or near the module 430. The insulating material shown with reference to FIGS. 7 and 8 is opaque (though other kinds of insulating materials are possible), thus allowing visibility into the components of the module 430 covered by the insulating material. FIG. 7 is a view of a top surface of the module of FIG. 6 in accordance with one embodiment. As seen with reference to FIG. 7, the solid-state defibrillation waveform therapy generator 406 can be located near the top internal surface of the module 430, thus being still inside the module 430 and being potted within the insulating material. The opposite internal side of the module can house additional components, such as components for at least one of vital sign monitoring, actigraphy, and motion or environmental information sensing, though other kinds of components are also possible. FIG. 8 is a bottom of the module 430 of FIG. 6 in accordance with one embodiment. The bottom surface of the module 430 (which is still inside the module 430) can include multiple components that are covered with the insulating material, such as one or more analog-to-digital converters (ADCs) 433, drivers and bias generating components 434 described above, an ECG frontend 435, as well other components, such as an actigraphy sensor, thoracic impedance sensor, environmental and motion sensors, and other vital signals and environmental sensing components. Further, this side of the module can include a control interface 436 interfaced to other components of the AED through the contacts.

As can be seen with reference to FIGS. 6-8, in addition, to relaxing requirements for dielectric spacing between components of the AED, the use of the isolated module 430 allows to stack the components vertically (thus decreasing spacing requirements), and also simplifying the manufacturing process for an AED including such a module 430.

The defibrillation circuit provides a defibrillation waveform or "pulse." In a further embodiment, pulse generation circuit 88 of the embodiments of FIGS. 3-5 can further include a polarity reversal correction circuit to ensure proper shock delivery in the event that the electrode pads 85*a-b* are improperly reversed. As further described, depending on the success of the delivery of the shock, polarity could automatically be reversed on the third defibrillation shock, as reversing polarity can aid in defibrillation of difficult cases. In addition to providing control of the waveform, the MCU 71 can further monitor the defibrillation waveform through the sensing circuit 87 and adjust the control and waveform based on the monitoring.

Figure 9:
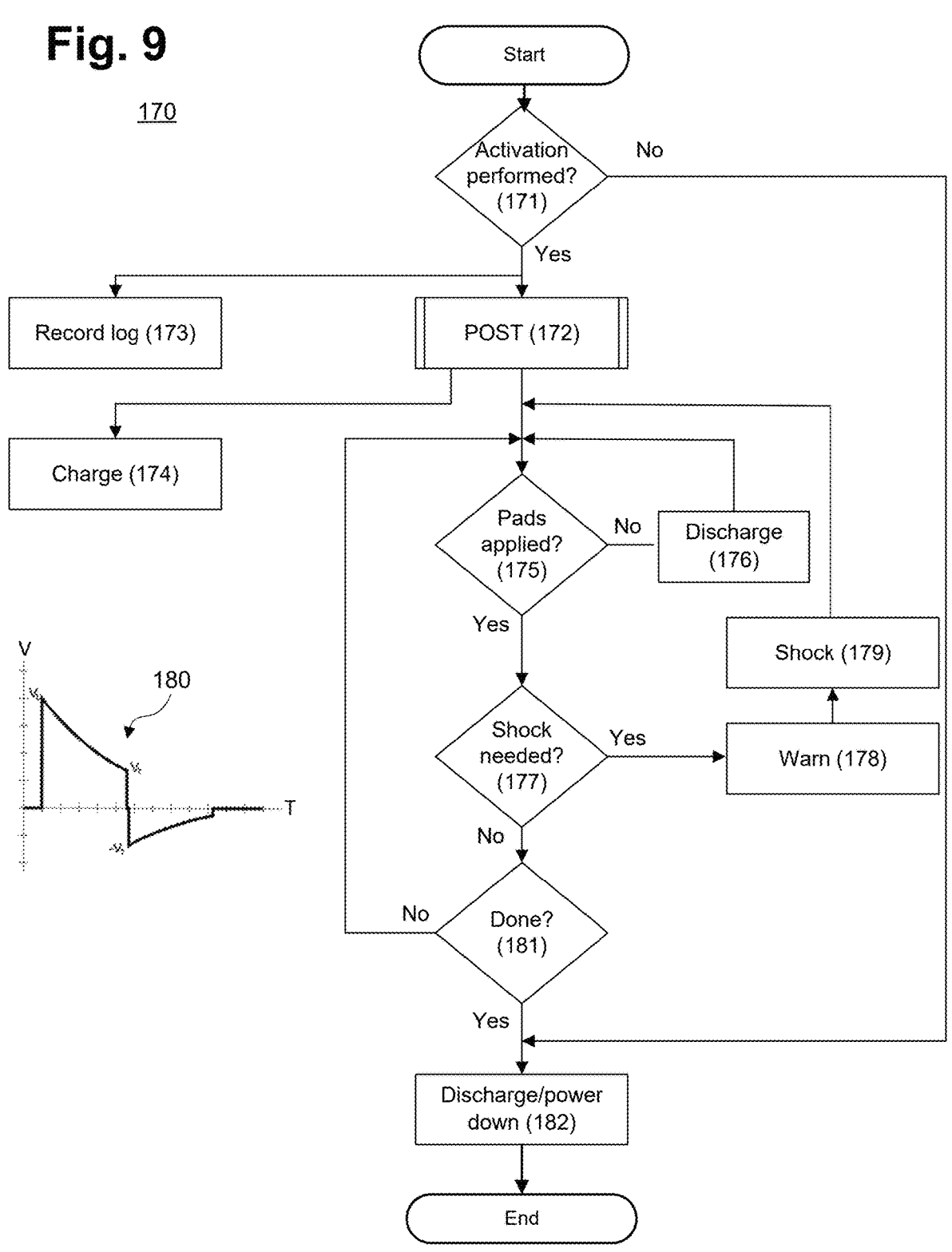
FIG. 9 is a flow chart showing a method for operating a disposable pocketable AED in accordance with one embodiment.

A disposable pocketable AED using the pulse generation circuit 88 is intended to be available at all times and easy to use with little to no training required. FIG. 9 is a flow chart showing a method 170 for operating a disposable pocketable AED in accordance with one embodiment. To start, the AED is activated (step 171) by the user pressing the "On" switch, removing the outer wrapping, opening the case or similar control, after which the AED executes a power-on self-test (POST) (step 172).

Following successful POST (step 172), both a record of the AED's activation is made in an onboard log (step 173) and the pulse capacitor 81*b* may be optionally pre-charged to a conservative level (step 174) by the high-voltage charging circuit 81*a*. The state of the electrode pads is determined (step 175). If the pads are not correctly applied (step 175), such as because the user of the AED has removed the pads from the victim 18, any energy generated for delivery of the shock is dissipated as described above, such as by activating the waveform generator 406 in the transconductance range under the control of the MCU 71 (step 176), which either ends the method 170 or returns the method to step 175, depending on the actions of the user.

If the pads are correctly applied, the AED determines whether a shockable rhythm is present (step 177). Provided a shockable rhythm is sensed (step 177), the AED issues a warning to the user (step 178) and a defibrillation shock is delivered (step 179). The defibrillation shock is delivered as a high voltage therapeutic waveform 180, preferably as a biphasic waveform, such as a biphasic truncated exponential (BTE), pulsed biphasic, and rectilinear biphasic waveform, modified biphasic, arbitrary or, alternatively, as a monophasic waveform. Other defibrillation waveforms are possible. Once the shock has been delivered, the device determines whether a normal rhythm has been restored and, if so, the methodology is done (step 181) and the AED will discharge the pulse capacitor 81*b* and power down (step after 15 minutes of a non-VF rhythm (182), ending the method 170. In some cases, several defibrillation shocks are required and the AED delivers biphasic defibrillation shocks, where the initial energy level for defibrillation begins at 120 J and either repeats or escalates for the second and subsequent defibrillation shocks up to a maximum of 360 J. In the use of escalation, the defibrillation energy is automatically adjusted by the AED with each subsequent defibrillation shock. In a further embodiment, based on the findings of a detection algorithm performed by the MCU 71 revealing success or failure of preceding defibrillation shocks the polarity of the defibrillation shock is reversed on the third shock (or any subsequent shock following the first shock) should no restoration of a non-shockable rhythm occur. In a further embodiment, the AED can automatically limit the number of shock re-attempts permitted, as after three defibrillation shocks, resuscitation of the victim 18 becomes unlikely.

In a further embodiment, as part of the process of delivering the defibrillation shock (step 179), the AED measures patient impedance during application of the defibrillation shock through the sensing circuit and adjusts one or more of the energy, voltage, and pulse width of the defibrillation waveform 180 in real time to generate optimal defibrillation therapy, where the x-axis represents time (T) and the y-axis represents voltage (V). Knowledge of patient impedance is crucial in a traditional design, which is used to determine the energy required to pre-charge the high-voltage pulse capacitor 81*b* to an appropriate level and to aid in realizing an appropriate energy deliver waveform. In practice, patient impedance changes during the shock, so conventional impedance-based pre-charge circuits have limited usefulness in achieving effective defibrillation. For instance, the impedance of a ten-year-old child is around 20 Ohms, whereas a 200-pound, middle-aged male has an impedance of about 75 Ohms. For both individuals, a waveform of 10 msec is likely necessary for effective defibrillation but their defibrillation energy and pre-charge parameters are significantly different. Moreover, impedance on the skin's surface typically decreases as defibrillation therapy progresses. Optionally the MCU 71 (shown in FIG. 2) interfaces to the sensing circuit to continually measure impedance in real time and adjusts parameters in the high voltage energy delivery module 79, voltage and pulse width (duration). Other parameters are possible.

For instance, an exemplary biphasic waveform is defined with an asymmetrical 65% tilt from a leading-edge voltage VL and trailing edge voltage VT/−VT with a polarity reversal halfway through the waveform. Patient impedance can affect the duration of the waveform where increased impedance means longer pulse width, lower voltage, or less energy to the heart, and decreased impedance means shorter pulse width, higher voltage, or more energy to the heart (unless patient impedance changes after the impedance is sensed). The most efficacious way to ensure correct energy delivery is to monitor and adjust the therapy in real time. One or more of these parameters can be adjusted by the MCU in real time to alter the amount of primary of the shock to reflect the ideal target therapy represented by the biphasic waveform.

Figures 10, 11, 12, 13, 14:
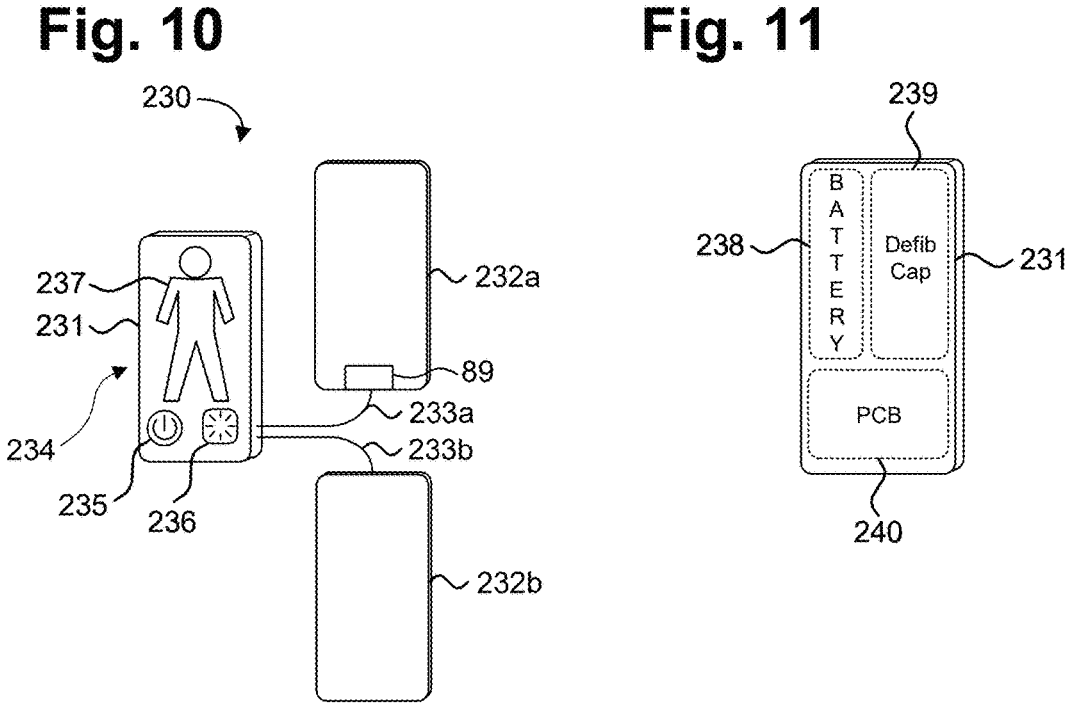
FIG. 10 is a front view showing a disposable single use pocketable AED with dual free-floating electrodes in accordance with one embodiment.
FIG. 11 is a cut-away view showing block component groups contained within the disposable single use pocketable AED of FIG. 10.
FIG. 12 is a side view showing the disposable single use pocketable AED of FIG. 10 with the housing and dual free-floating electrodes stowed in a carrying case.
FIG. 13 is a side view showing the disposable single use pocketable AED of FIG. 10 with the housing and dual free-floating electrodes partially deployed from the carrying case.
FIG. 14 is a back view showing the cable management system of the disposable single use pocketable AED of FIG. 10.

FIG. 10 is a front view showing a disposable single use pocketable AED with dual free-floating electrodes in accordance with one embodiment. The AED 230 combines a highly portable form factor with the charging circuit 88 that deliver defibrillating energy out of only modest lightweight battery capacity. Such a pocket-sized AED can be made readily available not just in the home, but anytime and anywhere that a would-be rescuer happens to be. The AED 230 advantageously uses the charging circuit 88, as discussed supra with reference to FIG. 3 et seq., to generate the bias voltage driving the waveform generator 406. This innovation allows the circuit to be powered with a low cost and lightweight battery and the high voltage charger circuit 81a and pulse capacitor 81b to be down-rated from the high capacitance levels utilized in conventional designs, all of which significantly decreases cost and size, thereby making single-use and device disposability possible.

The AED 230 is housed in a small lightweight housing 231, about the size and weight of a mobile telephone, that is, in the range of 2.25 to 3.5 inches wide, 5.25 to 7 inches tall, and 0.25 to 1.0 inches deep and a weight in the range of 130 to 550 grams. Other sizes and form factors are possible. The pair of free-floating electrodes 232a-b are connected to the housing 231 by a pair of flexible leads 233a-b. The charging circuit 88 as described above is interfaced to the electrodes 232a, b. Each electrode 232a-b is coated with an adhesive hydrogel that ensures proper contact with the victim's skin. The electrodes 232a-b are for a single-use only. The front of the AED 230 has a user interface 234 designed to optimize user understanding that includes a set of visual instructions 237. Optionally, the AED 230 can be equipped with a speaker (not shown) to generate voice prompts.

The AED 230 includes a streamlined and simple user interface that facilitates understanding and proper use during an emergency by lay people. Power is controlled by a simple "On" switch 235 and the status of the AED 230 is intuitively provided by a visual indicator 236 that changes color depending upon the state of the AED, for instance, through a display of "red," "yellow" and "green" to respectively indicate device activated but not attached to the patient, device attached and pulse capacitor 81b charging, and a ready-to-shock condition. Other colors, forms and types of indicators are possible. Other information, such as impedance and voltage, vital signs, thoracic activity, actigraphy, motion or environmental information, as well as other information can similarly be provided to the user interface or recorded for later analysis. In a further embodiment, the AED 230 includes mobile communications capabilities by which to automatically summon medical assistance, generally by calling 9-1-1 or the equivalent in most localities, upon the sensing of a shockable rhythm. The mobile communications capabilities integrated into the AED 230 by including appropriate circuits and components or through a special features module providing the mobile communications capabilities to the AED. The AED could also receive mobile communications capabilities through a wireless interface, such as WiFi or Bluetooth, over which the AED can communicate to a mobile phone or wide area network, such as the Internet, and relay a 9-1-1 call. Alternatively, a mobile phone or device could be supplemented with the features of the AED 230.

FIG. 11 is a cut-away view showing block component groups contained within the disposable single use pocketable AED 230 of FIG. 10. The AED's circuit is provided on a printed circuit board (PCB) 240 contained within the housing 231, which also contains a low-cost, high-energy density battery 238 (optionally, a primary cell) and a pulse capacitor 239.

FIG. 12 is a side view showing the disposable single use pocketable AED 230 of FIG. 10 with the housing and dual free-floating electrodes stowed in a carrying case 242. The AED 230 is intended to be easily carried in a pocket and could be carried in a purse, backpack, glovebox, golf bags, and so forth, so as to enable the AED 230 to be conveniently on-hand in case of an SCA situation in the same manner that most people have their mobile phone on-hand.

FIG. 13 is a side view showing the disposable single use pocketable AED 230 of FIG. 10 with the housing and dual free-floating electrodes partially deployed from the carrying case 242. The pair of free-floating electrodes 232a-b share a similar front profile with the housing 231. The housing 231 and electrodes 232a-b slide out of the carrying case 242 when being deployed.

FIG. 14 is a back view showing the cable management system 241 of the disposable single use pocketable AED 230 of FIG. 10. A cable management system 241 is used to store the leads 232a-b inside of the housing 231, where the leads are internally retracted by the smart cable management system 241 until needed.

One of the dual free-floating leads 232a-b can be eliminated by providing an electrode pad surface on the AED's housing. FIG. 15 is a front view showing a disposable single use pocketable AED 250 with a single free-floating electrode 252 in accordance with one embodiment. As before, the AED 250 is housed in a small lightweight housing 251, but only one free-floating electrode 252 is connected to the housing 31 by a single flexible lead 253.

FIG. 16 is a rear view showing the integrated electrode 258 of the disposable single use pocketable AED 250 of FIG. 15. An integrated electrode pad 258 is provided on a rear-facing surface of the housing 251. A planar laminated high energy pulse transformer is incorporated into each electrode 252, 258, as further discussed infra with reference to FIG. 19. Both the single free-floating electrode 252 and integrated electrode 258 are coated with an adhesive conductive hydrogel that ensures proper contact with the victim's skin. The front of the AED 250 similarly has a user interface 254 designed to optimize user understanding that includes a set of visual instructions 257. Optionally, the AED 250 can be equipped with a speaker (not shown) to generate voice prompts. Power is again controlled by an "On" switch or optionally an activation circuit 255 and the status of the AED 250 is provided by a visual indicator 256. The AED's circuit is provided on a PCB (not shown) contained within the housing 251, which also contains a low-cost, high-energy density battery (not shown) and pulse capacitor (not shown).

FIG. 17 is a side view showing the disposable single use pocketable AED 250 of FIG. 10 with the housing 251 and single free-floating electrode 252 stowed in a carrying case. The single free-floating electrode 252 shares a similar profile with the housing 251.

FIG. 18 is a side view showing the disposable single use pocketable AED of FIG. 10 with the housing and single free-floating electrodes partially deployed from the carrying case. The housing 251 and electrode 252 slide out of the carrying case 260 when being deployed. A smart cable management system (not shown) is also used to store the single lead 253 inside of the housing 251, where the lead is internally retracted by a cable management system until needed.

FIG. 19 is a top view diagram showing an electrode pad assembly 271 for use in the disposable single use pocketable AEDs 230, 250 of FIGS. 10 and 15. Each electrode contains an embedded planar laminated high energy pulse transformer. This type of transformer exhibits high power density by functioning at high switching frequencies, while packaged in a low profile with larger surface area, thereby preventing overheating. In each electrode assembly 271, a primary winding 272 and a secondary winding 273 are laminated together into a planar transformer 270 with a jumper that is soldered, welded, crimped, or otherwise electrically conducted together.

The circuits described herein provides the basis for external defibrillators that are easy to carry, low cost and lightweight, while delivering a high-voltage, high-energy biphasic shock suitable for cardiac defibrillation and victim resuscitation. External defibrillators utilizing this circuit can help to facilitate the widespread adoption of the portable defibrillation technology and thereby meaningfully help to decrease the number of deaths from sudden cardiac arrest. Moreover, such circuits could also aid in reducing size and cost of implantable defibrillators.

In a further embodiment, the circuits described herein, including the circuits described with reference to FIGS. 3-5, could be incorporated into an implantable cardioverter defibrillator (ICD). In a still further embodiment, the circuits could be incorporated into a wearable external defibrillator.

The descriptions of the AED and circuits above can be combined with the features described in the following commonly-owned patent documents: U.S. Pat. No. 11,794,026, issued Oct. 24, 2023; U.S. patent application Ser. No. 18/401,199, filed Dec. 29, 2023; U.S. patent application Ser. No. 18/486,992, filed Oct. 13, 2023; and U.S. patent application Ser. No. 18/806,588, filed Aug. 15, 2024. The entire disclosures of all of these four patent documents are hereby incorporated by reference. While the invention has been particularly shown and described as referenced to the embodiments thereof, those skilled in the art will understand that the foregoing and other changes in form and detail may be made therein without departing from the spirit and scope of the invention.

What is claimed is:

1. A defibrillator, comprising:

one or more power generation subcircuits configured to generate a variable voltage bias supply;

a solid-state defibrillation waveform therapy generator circuit comprising a plurality of elements at least portion of which is configured to be driven by the variable voltage bias supply, the solid-state defibrillation waveform therapy generator circuit configured to:

generate one or more defibrillation waveforms that are conducted to a patient when the variable drive bias voltage supply is in a high energy state, activating at least some of the elements of the solid-state defibrillation waveform therapy generator in a saturated region; and generate one or more internal discharge waveforms that are isolated from the patient when the variable drive bias voltage supply is in a low energy state, activating at least some of the elements of the solid-state defibrillation waveform therapy generator in a transconductance region and dissipating energy as heat; and a microcontroller control unit configured to control whether the variable voltage bias supply is provided to the solid-state defibrillation waveform therapy generator circuit at the high energy state or at the low energy state.

2. A defibrillator according to claim 1, the activation of the at least some of the elements of the solid-state defibrillation waveform therapy generator in the transconductance region is sequential.

3. A defibrillator according to claim 1, wherein the activations of one or more of the elements of the solid-state defibrillation waveform therapy generator in at least one of the transconductance region and the saturated regions are sequential.

4. A defibrillator according to claim 3, wherein a pause follows each of the activations to allow for safe dissipation of the heat.

5. A defibrillator according to claim 1, further comprising:

a pulse capacitor configured to provide at least a portion of the energy used by the solid-state defibrillation waveform therapy generator circuit;

a voltage regulator configured to regulate voltage of the energy that is provided from the pulse capacitor to the solid-state defibrillation waveform therapy generator circuit.

6. A defibrillator according to claim 5, further comprising:

one or more power generation sub-circuits configured to receive control signals from the microcontroller control unit, wherein one of the power generation sub-circuits is further configured to control the voltage regulator.

7. A defibrillator according to claim 6, wherein the regulation by the one or more power generation sub-circuits provides a bias voltage at a higher or at a lower potential than positive and negative connections of the pulse capacitor or patient connection.

8. A defibrillator according to claim 5, wherein the microcontroller control unit is configured to make a determination to dissipate at least a portion of the energy into the heat through the activation of at least some of the elements in the transconductance region.

9. A defibrillator according to claim 8, further comprising:

a sensing circuit configured to sense a presence or absence of a shockable rhythm in a patient, wherein the microcontroller control unit makes the determination based on the absence of the shockable rhythm.

10. A defibrillator according to claim 8, wherein the determination is made due to a defibrillator powering down by a switch interfaced to the microcontroller control unit.

11. A defibrillator according to claim 8, further comprising:

a pulse capacitor configured to provide at least a portion of the energy used by the solid-state defibrillation waveform therapy generator circuit;

a high voltage charger circuit interfaced to the microcontroller control unit 6 and configured to charge the pulse capacitor;

wherein the determination is made based on a time necessary for the charging of the pulse capacitor by the high voltage charger circuit.

12. A defibrillator according to claim 8, wherein the determination is made due to a command to abort delivery of the one or more defibrillation waveforms.

13. A defibrillator according to claim 1, wherein the microcontroller control unit controls a polarity of the one or more defibrillation waveforms by controlling which of the elements are open and closed during the generation of those defibrillation waveforms.

14. A defibrillator according to claim 13, wherein the microcontroller control unit reverses a polarity of one or more of the defibrillation waveforms based on a result of delivery of earlier ones of the defibrillation waveforms.

15. A defibrillator according to claim 13, wherein the solid-state defibrillation waveform therapy generator circuit further is configured to generate three of the defibrillation waveforms and the polarity of the third defibrillation waveform is opposite to the polarity of the first and second defibrillation waveforms.

16. A defibrillator according to claim 13, further comprising:

two pads through the which the defibrillation waveforms are configured to be delivered to a patient; and a polarity reversal correction circuit configured to ensure proper defibrillation waveform delivery upon placement of the pads on the patient being reversed.

\* \* \* \* \*